United States Patent [19]

Sedlak et al.

[11] Patent Number: 5,733,041
[45] Date of Patent: Mar. 31, 1998

[54] METHODS AND APPARATUS FOR ELECTRICAL CONNECTION INSPECTION

[75] Inventors: John Michael Sedlak, Fort Wayne; David Michael Prough, Leo, both of Ind.

[73] Assignee: General Electric Company, Fort Wayne, Ind.

[21] Appl. No.: 550,620

[22] Filed: Oct. 31, 1995

[51] Int. Cl.⁶ .................................................. G01N 25/72
[52] U.S. Cl. ............................... 374/45; 374/5; 374/152
[58] Field of Search .............................. 374/45, 5, 152

[56] References Cited

U.S. PATENT DOCUMENTS

| | | |
|---|---|---|
| 3,463,007 | 8/1969 | Jones et al. . |
| 3,803,413 | 4/1974 | Vanzetti et al. . |
| 4,214,164 | 7/1980 | Traub et al. . |
| 4,620,799 | 11/1986 | Palazzetti et al. . |
| 4,792,683 | 12/1988 | Chang et al. . |
| 4,854,724 | 8/1989 | Adams et al. . |
| 4,999,499 | 3/1991 | Bhatt . |
| 5,052,816 | 10/1991 | Nakamura et al. . |
| 5,064,291 | 11/1991 | Reiser . |
| 5,080,279 | 1/1992 | Davison . |
| 5,201,841 | 4/1993 | Lebeau et al. . |
| 5,208,528 | 5/1993 | Quintard . |
| 5,246,291 | 9/1993 | Lebeau et al. . |
| 5,250,809 | 10/1993 | Nakata et al. . |
| 5,407,275 | 4/1995 | Long . |
| 5,422,498 | 6/1995 | Nikawa et al. ............ 374/45 X |

Primary Examiner—Hezron E. Williams
Assistant Examiner—Joseph L. Felber
Attorney, Agent, or Firm—Enrique J. Mora

[57] ABSTRACT

Apparatus and methods for inspecting electrical connections so as to determine the presence of fault connections between magnet wires and power leads are described. The apparatus includes a processing unit, a power supply unit, and a temperature sensing unit. The processing unit includes a programmable logic controller (PLC) having a central processing unit (CPU) and a plurality of input and output slots. The power supply unit includes a power lead connector configured to couple to the motor power leads and a power relay coupled to the PLC. The temperature sensing unit includes infrared thermometers to determine the temperature at the electrical connections between the stator magnet wires forming the motor windings and the power leads. The outputs of the thermometers are coupled to the programmable logic controller (PLC).

28 Claims, 3 Drawing Sheets

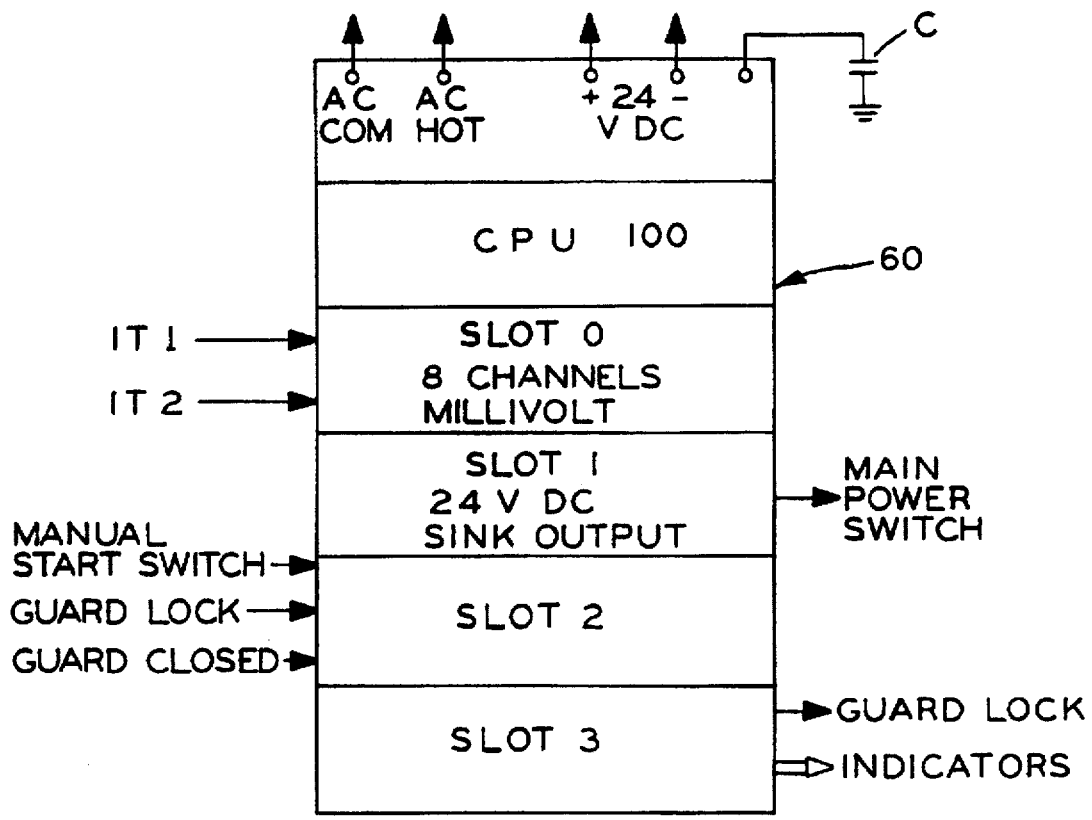
FIG_4
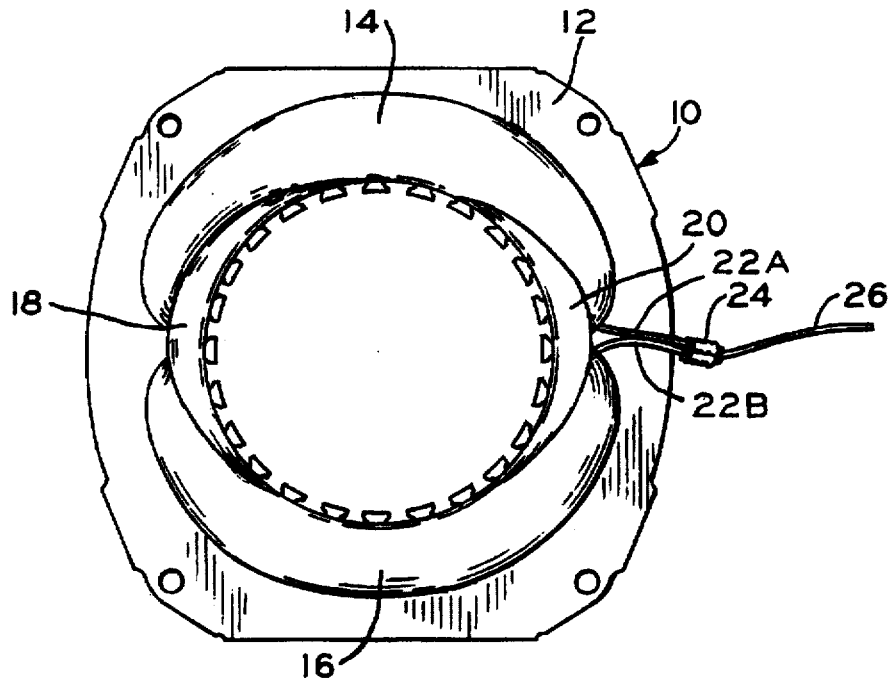
FIG_1

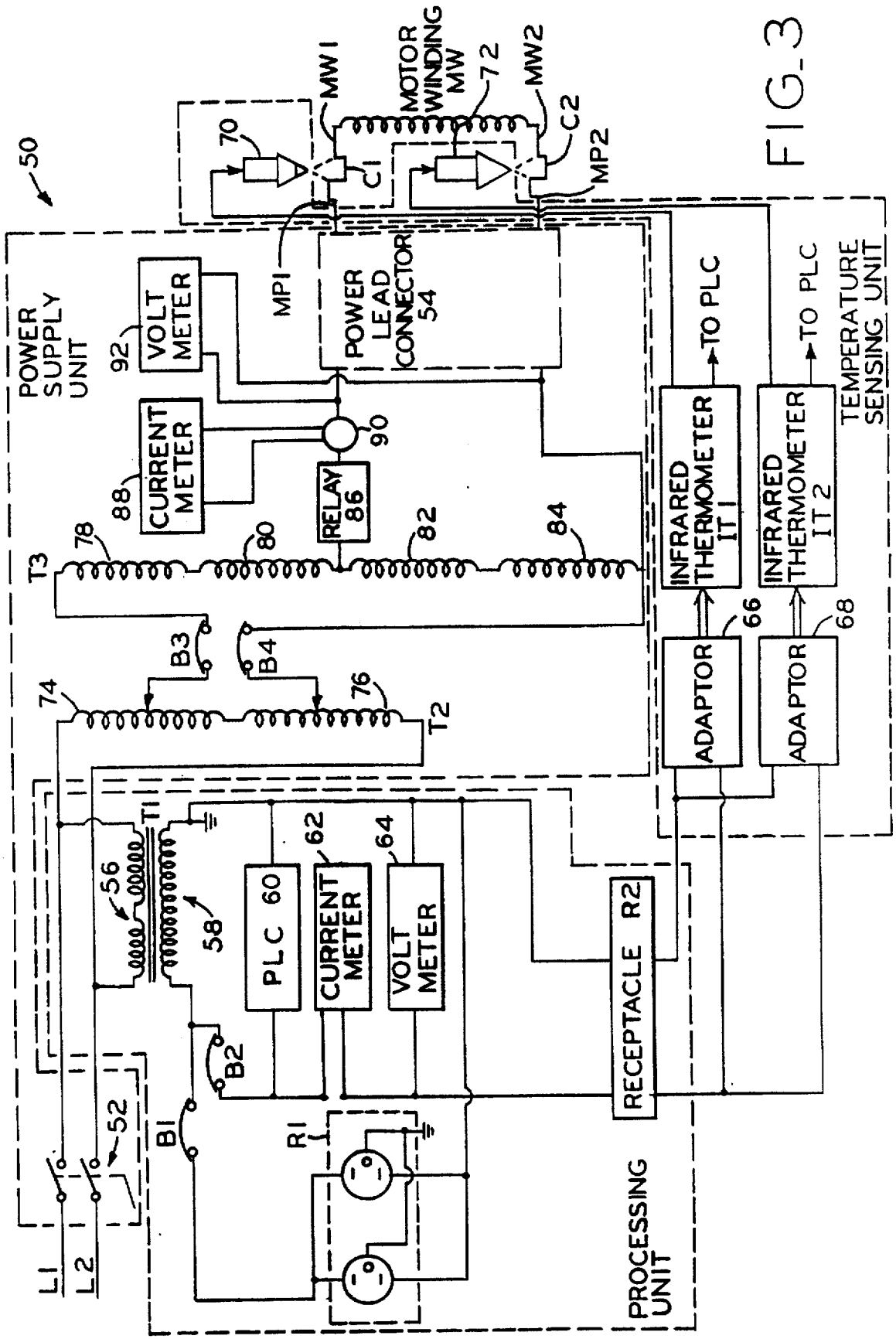
FIG_3

METHODS AND APPARATUS FOR ELECTRICAL CONNECTION INSPECTION

FIELD OF THE INVENTION

This invention relates generally to inspecting an electrical connection, or splice, between a power lead and a magnet wire and, more particularly, to methods and apparatus which may be utilized in determining the acceptability of such a splice.

BACKGROUND OF THE INVENTION

Dynamoelectric machines, such as motors and generators, typically include a magnetic core having a plurality of windings formed from magnet wire. For example, in one particular configuration, an electric motor includes a stator core having a stator bore. Side portions of a plurality of stator windings formed by the magnet wire are inserted into stator core slots having open ends at the periphery of the stator bore, and each end of the magnet wire extends from the stator core and is electrically connected, or spliced, to at least one power lead.

Magnet wire of a stator typically has a tough enamel coating. Such coating may enhance motor performance, for example, by electrically insulating each winding turn from other winding turns and protecting the magnet wire against damage which may cause reduced operational efficiency due to increased resistance of the magnet wire and possibly even short circuiting of the wire.

Although the enamel coating may enhance motor operation, such coating generally presents difficulties when attempting to form a reliable electrical connection, or splice, between a magnet wire and a power lead. For example, even though the insulation at the ends of the power leads may be stripped away so that the power lead conducting wires are exposed, it is time consuming and difficult to remove a segment of the enamel coating from each end of the magnet wires.

To reduce the time required to make electrical connections between stator magnet wires and power leads, a connector formed of electrically conducting material may be utilized. One known connector is, for example, substantially U-shaped and has a plurality of sharp serrations formed in the connector material on the interior surface of the connector. The stripped end of at least one power lead and one end of an enamel coated magnet wire may be placed within the interior of the U-shaped connector. A crimper may then fold the legs of the connector over the ends of the magnet wire and power lead, and may also squeeze, or crimp, the connector so that the sharp serrations are forced through the magnet wire enamel coating and into electrical contact with the magnet wire. Such crimping of the connector also may ensure that the connector is in electrical contact with the conducting wire at the stripped end of the power lead. An insulating sheath, which may be formed of heat-shrinkable insulating material, may then be placed over the crimped connector and heated so that the sheath shrinks and grips the connector.

Although the above described connector and crimping process generally form an acceptable electrical connection, or splice, between the magnet wire and power lead, there is a possibility that the magnet wire may "float-up", or move within the connector toward the open end of the connector legs, during the crimping process. As a result, the serrations may not make good electrical contact with the magnet wire. For example, the serrations may not extend fully through the enamel coating and into firm contact with the magnet wire.

If good electrical contact is not made between the magnet wire and the connector, motor performance may be adversely affected, for example, due to increased resistance and power loss at the connector.

Further, since manufacturing limitations may prevent high magnitude current stator winding testing, a bad electrical connection between a magnet wire and a power lead may not necessarily be detected until the motor actually is put in the field. High current testing generally is not performed on stator windings since such testing itself could damage the magnet wire. Also, even though a stator may pass low current tests at the manufacturing site, the vibrations and normal external conditions which a motor is exposed to during shipping may further deteriorate a bad electrical connection. As a result, the motor may not pass even low current tests when performed at the delivery site.

Early detection of bad electrical connections, especially prior to delivery, may facilitate reducing costs by avoiding costs associated with having motors deemed unacceptable at the delivery site or in the field due to bad electrical connections. Such early detection may also facilitate enhancing customer confidence.

With respect to the detection of unacceptable electrical connections, since such detection may be performed at a manufacturing site, it would be preferable to provide a manner of detecting such unacceptable connections which does not require substantial training and can be easily performed. In addition, rather than a mere qualitative, e.g., bad or good, measurement, a quantitative measurement indicative of the nature of an electrical connection may be preferred. A quantitative measurement may be more suitable, for example, for statistical process control applications in a manufacturing setting. For example, depending on the quantitative temperature measurement, a harder crimp may be required to form an acceptable splice. Further, to avoid an unacceptable increase in manufacturing time, such detection preferably would be performed rapidly. Such rapid detection would be particularly crucial in high volume manufacturing operations.

Accordingly, it would be desirable to improve motor reliability by facilitating the identification, based on quantitative measurements, of unacceptable electrical connections between stator magnet wires and power leads. It would also be desirable and advantageous to identify such unacceptable electrical connections without significantly increasing the costs and time associated with manufacturing a stator.

An object of the present invention is to improve motor reliability by facilitating early identification, based on quantitative measurements, of potentially unacceptable electrical connections between stator magnet wires and power leads.

Another object of the present invention is to quickly, and at a low cost, identify such potentially unacceptable electrical connections.

Still another object of the present invention is to facilitate reducing costs by reducing the quantity of motors which may be returned due to unacceptable electrical connections between stator magnet wires and power leads.

Yet another object of the present invention is to facilitate enhancing customer confidence by better ensuring that reliable electrical connections are made between stator magnet wires and power leads in delivered motors.

SUMMARY OF THE INVENTION

These and other objects may be attained by apparatus and methods for inspecting electrical connections, or splices, between stator magnet wires and power leads which, in one embodiment of the apparatus, includes a processing unit, a power supply unit, and a temperature sensing unit. The processing unit, in one embodiment, includes a programmable logic controller (PLC) having a central processing unit (CPU) and a plurality of input and output slots. The power supply unit, in one embodiment, includes a power lead connector designed to interconnect the motor power leads and a power control relay. The relay is coupled to and controlled by the PLC. The temperature sensing unit, in one embodiment, includes infrared thermometers and probes for sensing the temperature at the electrical connections, or splices, between the stator magnet wires forming the motor windings and the power leads. The outputs of the thermometers are coupled to an input slot of the PLC.

In one form of operation, and to determine whether a particular electrical connection is unacceptable, i.e., to determine the presence of electrical connection faults, the temperature sensing probe is positioned sufficiently near the electrical connection to sense or measure temperature at the connection. The operator may then depress a manual start switch, and the PLC causes the power relay to close and the motor windings are energized. While the windings are energized, the temperature sensing unit generates electrical signals representative of the temperature at the electrical connection, and such signals are supplied to the PLC. The CPU compares the signals received from the temperature sensing unit with at least one predetermined value stored in a suitable memory element. The predetermined value represents an upper temperature limit for an acceptable connection.

If the sensing unit output signal is above the predetermined value, then the connection may be unacceptable and the PLC generates a fault signal to energize a fault indicator, e.g., a light emitting diode (LED), to alert the operator that an electrical connection fault, such as a bad splice, may have been identified. Except as noted below, if the sensor output signal is below the predetermined value, then the connection is determined to be acceptable and no fault signal is generated. If the sensor output signal is substantially unchanged from just prior to energization of the motor windings to the time at which the windings are energized, and even if the signal is below the predetermined value, then the connection may be unacceptable, e.g., an open circuit, and the PLC generates a fault signal.

The apparatus and methods described above improve motor reliability by facilitating the identification, based on quantitative measurements, of unacceptable electrical connections between stator magnet wires and power leads. Such apparatus and methods also enable identification of such unacceptable electrical connections without significantly increasing the costs associated with manufacturing a stator.

BRIEF DESCRIPTION OF THE DRAWINGS

FIG. 1 is a plan view of a motor stator including a connector forming an electrical connection, or splice, between stator magnet wires and a power lead.

FIG. 3 is a circuit schematic diagram of one embodiment of an electrical connection inspection circuit.

FIG. 4 is a block diagram illustrating, in more detail, one embodiment of a programmable logic controller which may be used in the inspection circuit illustrated in FIG. 3.

DETAILED DESCRIPTION

Figure 2A:
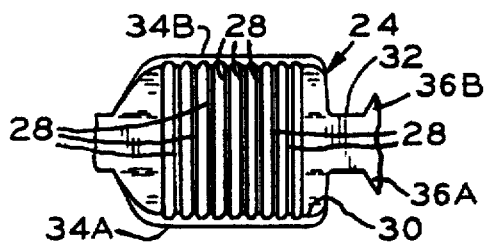
FIGS. 2A, 2B, 2C and 2D are plan, side, front (with parts cut-away) and cross-section views, respectively, of one embodiment of a connector which may be utilized to form an electrical connection between stator magnet wires and power leads.

FIG. 1 illustrates a stator 10 including a magnetic core 12 and windings 14, 16, 18 and 20. Windings 14, 16, 18 and 20, for example, are formed by magnet wires 22A and 22B which are coupled, at electrical connector 24, to a power lead 26. Magnet wires 22A and 22B may be coated with a tough enamel coating as hereinbefore described. If a good electrical connection is not made by connector 24 between magnet wires 22A and 22B and power lead 26, motor performance may be adversely affected due, for example, to increased resistance and power losses at connector 24.

FIGS. 2A, 2B, 2C and 2D illustrate one embodiment of electrical connector 24 which may be utilized to connect magnet wires 22A and 22B to power lead 26. As shown in FIG. 2A, which is a top plan view, connector 24 includes serrations 28 formed in an interior surface 30 thereof. Connector 24 also includes an alignment portion 32 in which the magnet wires and power lead may be inserted so that the magnet wires and power lead are aligned with serrations 28.

Figure 2B:
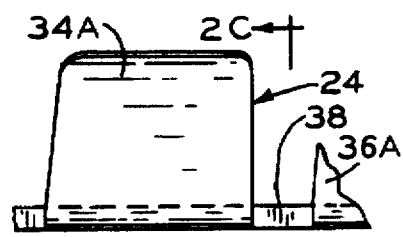

FIG. 2B is the side view of connector 24 and shows one leg 34A which has serrations 28 (FIG. 2A) formed on an interior surface thereof and an alignment leg 36A. Connector 24 also includes a substantially planar lower portion 38. Of course, a segment of portion 38 which extends between legs 34A and 34B has serrations formed thereon. Prior to crimping, the magnet wires and power lead preferably lie on, or are positioned adjacent to, portion 38.

Figure 2C:
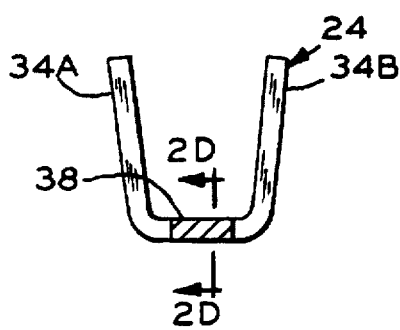

FIG. 2C is a view of connector 24 through line 2C—2C in FIG. 2B. As shown in FIG. 2C, connector 24 is substantially U-shaped. Legs 34A and 34B may be folded over and crimped, as hereinafter described.

Figure 2D:
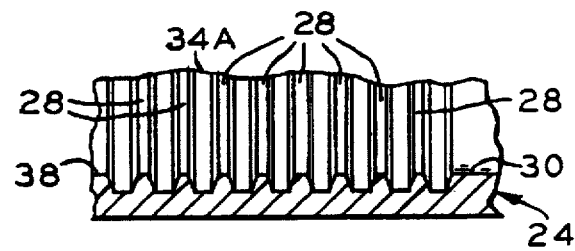

FIG. 2D is a cross-sectional view with parts cut-away of connector 24 through line 2D—2D shown in FIG. 2C. As clearly shown in FIG. 2D, serrations 28 extend from interior surface 30 of connector 24.

Of course, many other types of connectors may be utilized to make an electrical connection, or splice, between stator magnet wires and power leads. Connector 24 is illustrated herein by way of example only. The inspection apparatus and methods described herein may be practiced with many other different types of connectors, and are not limited to use with connector 24.

FIG. 3 is a schematic diagram illustrating one embodiment of an electrical connection, or crimp, inspection apparatus 50 which facilitates the early identification or detection of unacceptable electrical connections between stator magnet wires and power leads. Inspection apparatus 50, in the illustrated embodiment, includes a master power switch 52 coupled to power lines L1 and L2 and a power lead connector 54 coupled to motor power leads MP1 and MP2. Motor power leads MP1 and MP2 are connected to stator magnet wire leads MW1 and MW2 of a motor winding MW, such as either of windings 14, 16, 18 or 20 (FIG. 1) at connectors C1 and C2. Electrical connectors C1 and C2 form electrical connections, or splices, between magnet wire leads MW1 and MW2 of motor winding MW and motor power leads MP1 and MP2. Connector 24 illustrated in FIGS. 2A–D, or other known connectors, may be utilized to make such electrical connections.

Although two connectors C1 and C2 are illustrated in FIG. 3, it is contemplated that fewer or more connectors could be utilized depending upon the particular stator configuration. In any event, the number of connections, or splices, inspected during any particular testing cycle may vary, depending for example upon the number of such splices for a particular stator and the number of such splices desired to be inspected. For example, a stator may have only one connector, or more than two connectors, and apparatus 50 may be configured to inspect all such connectors for a stator during one testing cycle.

It also is contemplated that a fixture may be constructed so that a plurality, e.g., thirty to forty, of stators could be loaded onto the fixture and oriented so that inspections may be made for all such stators using inspection apparatus 50. One stator represented as motor winding MW is shown in FIG. 3 for illustrative purposes only. Also, the fixture may be positioned within a safety cage so that the operator and others are prevented from accidentally contacting an energized stator during a testing cycle. Such a safety cage may include a guard gate having a solenoid-controlled lock which, as hereinafter explained, may be controllable by apparatus 50.

Continuing with the description of FIG. 3, inspection apparatus 50 includes a first transformer T1 for lowering 480 volts AC applied on its primary windings 56 to 115 volts AC output on its secondary winding 58. Secondary winding 58 of transformer T1 is coupled to a processing unit, shown as a programmable logic controller (PLC) 60. Secondary winding 58 also is coupled to a current meter 62 and a volt meter 64. Secondary winding 58 of transformer T1 also is coupled to duplex receptacles R1 and R2. Receptacle R2 is shown in block form and would be configured substantially similar to receptacle R1. Receptacle R1 may be used, for example, for energizing a portable computer for reading and loading a memory of PLC 60. Transformer T1 may be a 500 VA control power transformer. Current meter 62 may be a 5 Amp ammeter, and volt meter 62 may be a 600 VAC volt meter. Further details regarding PLC 60 are provided hereinafter.

The temperature sensing unit also is coupled, via receptacle R2, to secondary winding 58 of transformer T1 and includes infrared thermometers IT1 and IT2 electrically coupled to adapters 66 and 68, respectively. Adapters 66 and 68, which may be 110V AC adapters, are utilized to ensure that appropriate voltage level signals are supplied to thermometers IT1 and IT2. The temperature sensing unit also includes infrared sensing probes 70 and 72. Probes 70 and 72 transmit electromagnetic signals, such as infrared signals, to thermometers IT1 and IT2 so that thermometers IT1 and IT2 may generate, based on the probe transmitted infrared signals, temperature-indicative signals. Such temperature-indicative signals are supplied from thermometers IT1 and IT2 to PLC 60. Thermometers IT1 and IT2 may be Omega Model 0S22 infrared thermometers including probes 70 and 72, commercially available from Omega Engineering, Inc., P.O. Box 4047, Stamford, Conn. 06907-0047.

Each sensing probe 70 and 72 may be supported and held in place on the stator mounting fixture by a flexible, lamp-style gooseneck. The focus distance from each probe 70 and 72 to the respective electrical connector C1 and C2 may, for example, be about approximately 1.2 inches, which requires that the gooseneck be long enough to swing probes 70 and 72 clear of the fixture for loading of the stators. Depending upon the particular probe utilized, the distance from the probe to the splice may vary. Typically, the probe manufacturer specifies the preferred distance, i.e., focus distance, at which the probe lens should be positioned to obtain an accurate measurement.

If a safety cage is utilized as hereinbefore described, PLC 60, current meter 62 and volt meter 64 may be mounted within the safety cage and viewable from outside of the cage, even when the safety cage gate is closed. Of course, it is contemplated that the PLC 60 and meters 62 and 64 could be mounted outside the cage.

The power supply unit includes a second transformer T2, coupled to master power switch 52, having windings 74 and 76. Transformer T2 is a variable type transformer such as a 30 Amp 480/0-560 V Pac, and the output of variable transformer T2 is coupled to a transformer T3, which may be a 10 KVA power transformer. Transformer T3 includes four windings 78, 80, 82 and 84, and windings 82 and 84 are tapped so that a voltage level ranging from about 0 to 183 volts may be applied to a power control relay 86, which may be a commercially available solid state relay, such as relay Model Number D4875 available from Crydom, 6015 Obispo Ave., Long Beach, Calif. 90805. A current meter 88 is coupled, via current transformer 90, to an output of relay 86 and a volt meter 92 is connected across windings 82 and 84. Current meter 88 may be a 5 amp ammeter and current transformer 90 may have a 100:5 ratio. Volt meter 92 may be a 600 VAC volt meter. Current and volt meters 88 and 92 may be utilized to ensure an operator that an appropriate signal is supplied to energize motor winding MW via power lead connector 54. The form of connector 54 may, of course, vary depending upon the particular stator desired to be inspected. Connector 54 may, for example, include ejector style power terminals for coupling to motor power leads MP1 and MP2.

A plurality of circuit breakers B1, B2, B3 and B4, which may be 35 Amp 600 volt circuit breakers, are provided to protect the various components of apparatus 50 from damage. Of course, many other types of protectors may be utilized.

FIG. 4 is a block diagram illustrating, in more detail, one embodiment of programmable logic controller 60. Controller 60 may, for example, be PLC Model No. D3-05BOC, commercially available from PLC Direct By Koyo, 315 Allen Street, Cumming, Ga. 30130. Controller 60 includes a central processing unit (CPU) 100 and four slots labelled SLOT 0–3. CPU 100 may, for example, be a 3.7K word CPU. By way of example, SLOT 0 includes an 8 channel (millivolt) analog input. Output signals from infrared thermometers IT1 and IT2 which are representative of the temperatures sensed at connectors C1 and C2, for example, are supplied as analog inputs at SLOT 0. Such thermometer output signals are digitized by a suitable analog-to-digital convertor (not shown) and supplied to CPU 100 for further processing as hereinafter described.

SLOT 1 is a 24 volt DC sink output which is coupled to power control relay 86. More particularly, relay 86 is normally non-conducting or open. When an operator depresses a manual touch start switch, and if other preconditions are satisfied, a logic signal is supplied from SLOT 1, for a predetermined period of time under the control of CPU 100, to relay 86. The logic signal from SLOT 1, coupled with the 24V DC signal supplied by PLC 60 to relay 86, causes relay 86 to transition to its conductive state. When CPU 100 causes the logic signal from SLOT 1 to be low and cuts-off the 24V DC signal, relay 86 once again becomes non-conductive.

SLOT 2 has eight input lines for receiving 110 volt AC signals. Slot 2 receives inputs from, for example, a manual start switch, the guard gate lock and a guard gate closed status indicator. The signal levels on these input lines indicate the status of various switches and components and may be utilized by CPU 100 to control, for example, the energization of the stator windings. For example, CPU 100 may control the SLOT 1 logic signal so that such signal is "high" only if the inputs at SLOT 2 indicate that the guard gate is closed and locked after the manual start switch has been depressed.

SLOT 3 is made up of a 115 volt AC eight line output. Outputs from SLOT 3 are supplied, under the control of CPU 100, to a guard lock control solenoid and status indicators. The guard lock control solenoid may be utilized to prevent an operator from opening the guard gate of the safety cage while an electrical connection test in accordance with the present invention is in progress. The status indicators may include separate indicators for indicating that a test is in progress and a guard lock fault, e.g., if the lock on the safety cage door is not locked. Also, a respective indicator may be associated with each thermometer IT1 and IT2 to indicate whether an unacceptable electrical connection has been detected. Such indicators may be color coded LEDs, for example.

PLC 60 also electrode other elements such as electronic memory storage elements, e.g., ROM and RAM memory elements. Also, PLC 60 includes AC common (COM) and positive (HOT) connections to couple PLC 60 to an energy source. A stabilizing/filtering capacitor C is connected to a terminal of PLC 60 normally utilized for coupling PLC 60 to an extension rack. It is contemplated, of course, that many different types of programmable logic controllers may be utilized, and PLC 60 is just one of many PLCs that may be used.

In one form of operation of apparatus 50, and to inspect electrical connections, or splices, a plurality of stators may be loaded on the fixture within the safety cage. Probes 70 and 72 may then be positioned at the proper focus distance from, for example, connectors C1 and C2, respectively, for a particular stator to be inspected. The safety cage gate of the fixture is then closed and locked. Master power switch 52 also should be closed.

An operator may initiate the inspection by depressing the start switch coupled to SLOT 2 of PLC 60. After such start switch has been depressed, and if the guard gate is closed and locked as indicated by signals received at SLOT 2 of PLC 60, PLC 60 supplies a "high" logic signal from SLOT 1 to power relay 86. The 24V DC output from PLC 60 also is supplied to relay 86 so that relay 86 transitions from a non-conductive to a conductive state. CPU 100 enables such logic signal and a 24V DC output signal for a predetermined period of time, e.g., 8 seconds. It is contemplated that such 24V DC signal may also be applied to a control solenoid for a guard gate lock to maintain the guard gate closed and locked while the logic signal output from SLOT 1 is "high". The signal supplied to such control solenoid from SLOT 3 serves as a logic signal to enable such solenoid for the test period. Also, under the control of CPU 100, a signal output from SLOT 3 energizes a test in progress indicator, and such indicator remains "on" while the logic signal output from SLOT 1 is "high".

If the guard gate of the safety cage is not closed and locked when the start switch is depressed, then CPU 100 causes a signal to be supplied from SLOT 3 to the guard lock fault indicator while no logic signals are supplied from SLOT 1 to power relay 86 and from SLOT 3 to the guard gate lock control solenoid. As a result, relay 86 will remain open and motor winding MW will not be energized under such conditions.

If the predetermined conditions are satisfied and motor winding MW is energized, while power is applied to motor power leads MP1 and MP2, infrared probes 70 and 72 transmit infrared signals to thermometers IT1 and IT2. Thermometers IT1 and IT2 receive the transmitted infrared signals so as to generate analog electrical signals representative of the temperatures at connectors C1 and C2, respectively, and the analog signals are in turn supplied to SLOT 0 of PLC 60.

To determine whether connections formed by connectors C1 and C2 are acceptable, and in one exemplary embodiment of operation, CPU 100 compares such infrared thermometer input signals with predetermined values, stored in memory of PLC 60, to determine whether such signals are within a predetermined, acceptable range. If such signals are within an acceptable range, then no fault indicators are turned on by CPU 100 via SLOT 3. If a signal from a particular thermometer IT1 and IT2 is not within an acceptable range, then CPU 100, via SLOT 3, turns on a fault indicator associated with such thermometer IT1 and IT2.

In another embodiment, temperature differentials may be utilized to determine whether connections C1 and C2 are acceptable. Particularly, a temperature differential may be determined by first determining an ambient temperature at the electrical connections prior to energizing the associated motor winding. Infrared probes 70 and 72 may, for example, be used to obtain such ambient temperature, i.e., pre-energization measurement data. Then the motor winding is energized using, for example, a voltage magnitude of about seventy-five percent of the magnitude of the rated voltage for the subject stator. Of course, other voltage values and time periods may be utilized depending on the specific stator characteristics.

As the winding is energized, thermometers IT1 and IT2 supply temperature-representative signals to SLOT 0 of PLC 60. CPU 100 processes signals received from thermometers IT1 and IT2 by subtracting the value of the initial ambient temperature signal from the value of the sensed temperature signal to obtain a differential temperature value for each respective thermometer IT1 and IT2. CPU 100 then compares the differential temperature value with a predetermined value stored in PLC memory, and if the differential temperature value is less than the stored, predetermined value, no fault indicator is energized by a SLOT 3 output signal. However, if the differential temperature value is greater than the stored, predetermined value, then CPU 100 causes a signal to be output from SLOT 3 to energize a fault indicator associated with the thermometer supplying the respective sensed temperature signal to SLOT 0. Also, if the differential temperature value is approximately about equal to zero, then CPU 100 causes a signal to be output from SLOT 3 to energize a fault indicator associated with the thermometer supplying the respective sensed temperature signal to SLOT 0. Such a condition, i.e., when the differential temperature equals about zero, indicates an open circuit condition.

Figure 5:
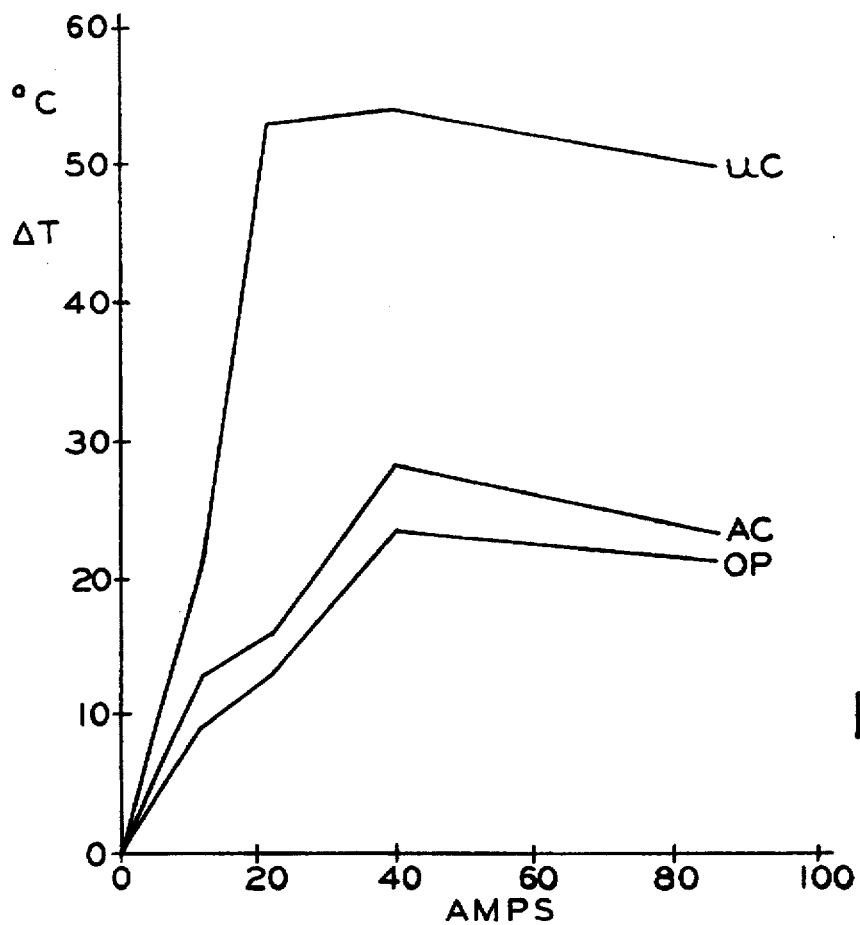
FIG. 5 is a graph illustrating temperature difference with respect to input current as measured at a motor overload protector and connectors using an infrared detector.

FIG. 5 is a chart illustrating input current (x-axis) versus temperature differential (y-axis) as measured with infrared thermometers for a particular motor. Line OP illustrates the measurements at an overload protector, line AC illustrates the measurements for an acceptable electrical connection, and line UC illustrates the measurements for an unacceptable electrical connection. As clearly shown in the diagram in FIG. 5, an unacceptable electrical connection exhibits a significantly higher temperature differential, even at low currents, as compared to an acceptable electrical connection. The overload protector temperature differential is provided only as a reference curve to facilitate an understanding of motor heating.

The predetermined stored values in the PLC memory may be obtained by measuring the temperature at an electrical connector which is known to be making a good electrical connection between a power lead and magnet wire. Of course, more than one such electrical connection could be inspected to determine an upper temperature differential limit. Once such an upper limit is so identified, the value of such limit is stored in the PLC memory and may be utilized by CPU 100 as described above.

Further, rather than using just one temperature value in making a binary, e.g., acceptable or unacceptable, type decision, different values can be utilized as indicators as to the acceptability of a particular connection. For example, a first value may be established to correlate to an acceptable connection. A second value may be established to correlate to a connection which may require further testing to determine whether such connection is acceptable. A third value may be established to correlate to an unacceptable connection.

Of course, it is contemplated that rather than utilizing temperature comparison or temperature differential values, temperature ratios or other values indicative of the temperature characteristics exhibited at the electrical connections when the windings are energized could similarly be determined by CPU 100 and utilized to identify unacceptable electrical connections.

With respect to the detection of unacceptable electrical connections between stator magnet wires and power leads with the apparatus and methods described above, use of such apparatus and methods do not require substantial training and can be quickly and easily performed. In addition, such apparatus and methods provide a quantitative measurement indicative of the nature of an electrical connection. Specifically, the analog signals supplied to PLC 60 by thermometers IT1 and IT2 are digitized and such digitized value may be stored in the PLC memory and readily accessible for use in, for example, statistical process controls for a crimping operation. For example, if a crimp is formed using a known force applied by the crimper to the connector, and if the resulting connection is unacceptable, in future crimping operations, a greater force may be determined to be necessary to form an acceptable connection. Further, the apparatus and methods enable identification of unacceptable connections after the stator has been fully assembled to sort such stators into separate groups based on the acceptability of such connections.

From the preceding description, it is evident that the objects of the invention are attained. Although the invention has been described and illustrated in detail, it is to be clearly understood that the same is intended by way of illustration and example only and is not to be taken by way of limitation. Accordingly, the spirit and scope of the invention are to be limited only by the terms of the appended claims.

What is claimed is:

1. A method for inspecting at least a first electrical connection between a first magnet wire forming a first winding on a stator core for an electric motor and at least a first power lead, said method comprising the steps of:
    energizing the first winding;
    sensing a temperature of the first electrical connection while the first winding is energized and while current flows through the connection; and
    determining whether the first electrical connection is acceptable based, at least in part, on the sensed temperature.

2. A method in accordance with claim 1 wherein the first winding is energized using a voltage having a magnitude of approximately about seventy-five percent of the magnitude of rated voltage.

3. A method in accordance with claim 1 further comprising the step of sensing a temperature of the first electrical connection prior to the first winding being energized.

4. A method in accordance with claim 3 wherein the step of determining whether the first electrical connection is acceptable comprises the steps of:
    determining a first connection temperature difference by subtracting the value of the sensed temperature of the first electrical connection prior to the first winding being energized from the value of the sensed temperature of the first electrical connection when the first winding was energized; and
    identifying the first electrical connection as unacceptable if the determined first connection temperature difference is not within a predetermined range.

5. A method in accordance with claim 1 wherein the first winding is energized for about eight (8) seconds.

6. A method in accordance with claim 1 wherein the step of sensing the temperature of the first electrical connection while the first winding is energized comprises the step of placing a first temperature sensor probe proximate the first electrical connection.

7. A method in accordance with claim 6 wherein the first temperature sensor probe comprises a first infrared sensor probe.

8. A method in accordance with claim 7 wherein the first infrared sensor probe has a focus distance of about 1.2 inches.

9. A method in accordance with claim 1 wherein at least a second electrical connection between a second magnet wire forming a second winding on the stator core and at least a second power lead is inspected by performing the steps of:
    while the second winding is energized, sensing a temperature of the second electrical connection; and
    determining whether the second electrical connection is acceptable based, at least in part, on the sensed temperature of the second electrical connection.

10. A method in accordance with claim 9 wherein the step of determining whether the second electrical connection is acceptable comprises the steps of:
    sensing a temperature at the second electrical connection prior to the second winding being energized;
    determining a second connection temperature difference by subtracting the value of the sensed temperature of the second electrical connection prior to the second winding being energized from the value of the sensed temperature of the second electrical connection when the second winding was energized; and
    identifying the second electrical connection as unacceptable if the determined second connection temperature difference is not within a predetermined range.

11. A method in accordance with claim 9 wherein the first and second windings are energized substantially simultaneously.

12. Apparatus for inspecting at least a first electrical connection through a first connector between a first magnet wire forming a first winding on a magnetic core and at least a first power lead, said apparatus comprising:
    a power supply unit for energizing the first winding and causing current to flow through the first electrical connection;
    a temperature sensing unit for generating a first signal representative of a temperature of the first electrical connector while the first winding is energized and while current flows through the first electrical connection; and a processing unit for determining whether the first electrical connection is acceptable based, at least in part, on the first signal.

13. Apparatus in accordance with claim 12 wherein said power supply unit comprises a power lead connector for connecting said apparatus to the first power lead, said power supply unit further comprising a power control relay.

14. Apparatus in accordance with claim 12 wherein said power supply unit further comprises a variable transformer, said power control relay being interconnected to said variable transformer and to said power lead connector.

15. Apparatus in accordance with claim 12 wherein said temperature sensing unit comprises a first infrared thermometer.

16. Apparatus in accordance with claim 15 wherein said temperature sensing unit further comprises a first temperature sensing probe electromagnetically coupled to said infrared thermometer.

17. Apparatus in accordance with claim 12 wherein said processing unit comprises a programmable logic controller.

18. Apparatus in accordance with claim 17 wherein said programmable logic controller comprises a central processing unit, said temperature sensing unit being coupled to said programmable logic controller to supply the first signal to said programmable logic controller, said central processing unit programmed to determine whether the first electrical connection is acceptable based, at least in part, on the first signal.

19. Apparatus in accordance with claim 17 wherein said programmable logic controller is coupled to said power supply unit to control said power supply unit to energize the first winding for a predetermined period of time.

20. Apparatus in accordance with claim 19 wherein the magnetic core comprises a stator core for an electric motor and said power supply unit energizes the first winding using a voltage having a magnitude of approximately about seventy-five percent of the magnitude of the rated voltage.

21. Apparatus in accordance with claim 17 wherein said temperature sensing unit senses a temperature at the first electrical connection prior to the first winding being energized and wherein said programmable logic controller is programmed to determine a temperature difference by subtracting the value of the sensed temperature of the first electrical connection prior to the first winding being energized from the value of the sensed temperature of the first electrical connection while the first winding was energized and to identify the first electrical connection as unacceptable if the determined temperature difference is not within a predetermined range.

22. Apparatus for inspecting at least first and second electrical connections between magnet wires forming windings on a magnetic core and power leads, said apparatus comprising:

a power supply unit for energizing the windings and causing current to flow through the first and second electrical connections, said power supply unit comprising a power control relay and a power lead connector for connecting to the power leads connected to the magnet wires;

a temperature sensing unit for generating first and second signals representative of first and second temperatures of the first and second electrical connections, respectively, while the windings are energized and while current flows through the first and second electrical connections, said temperature sensing unit comprising at least first and second probes for sensing the temperatures at the first and second electrical connections, respectively; and a processing unit for determining whether the first and second electrical connections are acceptable based, at least in part, on the first and second temperatures, said processing unit being coupled to the output of said temperature sensing unit and to a solenoid control of said power switch.

23. Apparatus in accordance with claim 22 wherein said power supply unit further comprises a variable transformer which may be adjusted by an operator, said variable transformer being coupled to said power control relay.

24. Apparatus in accordance with claim 22 wherein said first and second probes comprise respective infrared sensing probes, and said temperature sensing unit further comprises first and second infrared thermometers electromagnetically coupled to said first and second probes, respectively.

25. Apparatus in accordance with claim 22 wherein said processing unit further comprises a programmable logic controller, said programmable logic controller comprising a central processing unit, said temperature sensing unit being coupled to said programmable logic controller to supply first and second signals representative of the first and second temperatures of the first and second electrical connections, respectively, to said programmable logic controller, said central processing unit programmed to determine whether the first and second electrical connections are acceptable based, at least in part, on the first and second temperatures, respectively.

26. A method for determining whether a splice between a stator magnet wire and a power lead provides an acceptable electrical connection therebetween, said method comprising the steps of:

determining a first temperature representative of the temperature at the splice without any current flowing therethrough;

energizing the electrical connection by passing a current through the connection;

while passing an electrical current through the electrical connection, determining a second temperature representative of the temperature at the splice; and determining whether the splice is acceptable based, at least in part, on the first and second temperatures.

27. A method in accordance with claim 26 wherein the first and second temperatures are determined using an infrared temperature sensor.

28. A method in accordance with claim 26 wherein determining whether the splice is acceptable comprises the step of obtaining a differential temperature value by subtracting the value of the first temperature from the value of the second temperature, and comparing the differential temperature value with a predetermined acceptance value.

* * * * *